US010957436B1

(12) United States Patent
Aertker et al.

(10) Patent No.: US 10,957,436 B1
(45) Date of Patent: Mar. 23, 2021

(54) DEVICE FOR TRACKING MEDICATION ADHERENCE

(71) Applicant: Patch Technologies, Inc., San Antonio, TX (US)

(72) Inventors: Andrew Aertker, San Antonio, TX (US); Gavin Buchanan, San Antonio, TX (US)

(73) Assignee: Patch Technologies, Inc., San Antonio, TX (US)

( * ) Notice: Subject to any disclaimer, the term of this patent is extended or adjusted under 35 U.S.C. 154(b) by 0 days.

(21) Appl. No.: 17/021,427

(22) Filed: Sep. 15, 2020

Related U.S. Application Data (60) Provisional application No. 62/990,442, filed on Mar. 16, 2020.

(51) Int. Cl.
| | |
|---|---|
| *G16H 20/10* | (2018.01) |
| *A61J 1/14* | (2006.01) |
| *A61J 1/03* | (2006.01) |
| *G16H 40/67* | (2018.01) |
| *A61J 7/04* | (2006.01) |
| *G16H 40/40* | (2018.01) |

(52) U.S. Cl.
CPC ............. *G16H 20/10* (2018.01); *A61J 1/03* (2013.01); *A61J 1/1412* (2013.01); *A61J 7/0418* (2015.05); *G16H 40/67* (2018.01); *A61J 2200/70* (2013.01); *G16H 40/40* (2018.01)

(58) Field of Classification Search
CPC ........ G16H 20/10; G16H 40/67; G16H 40/40; A61J 1/1412; A61J 1/03; A61J 7/0418; A61J 2200/70
See application file for complete search history.

(56) References Cited

U.S. PATENT DOCUMENTS

| | | | | |
|---|---|---|---|---|
| 8,688,268 | B2 * | 4/2014 | Samain | B01F 13/1063 700/233 |
| 9,550,031 | B2 * | 1/2017 | Van Sickle | G16H 40/67 |
| 10,821,222 | B2 * | 11/2020 | Pananen | A61J 1/1481 |
| 2008/0218348 | A1 * | 9/2008 | August | G06Q 20/203 340/572.1 |
| 2014/0206976 | A1 * | 7/2014 | Thompson | A61B 5/0024 600/391 |
| 2014/0341411 | A1 * | 11/2014 | Mohindra | A61J 7/0436 381/334 |
| 2016/0367188 | A1 * | 12/2016 | Malik | G16H 40/67 |

* cited by examiner

*Primary Examiner* — Michael Collins
(74) *Attorney, Agent, or Firm* — Shah IP Law, PLLC (57) ABSTRACT

A medication adherence tracking device is configured for being attached to a cap of a conventional medication container. The tracking device includes an adhesive layer for attaching the device to the cap. The device also includes an infrared proximity sensor for detecting an amount of light that is reflected by a wall surface and/or a bottom surface of the medication container. A transmitter of the tracking device transmits adherence data to an external computing device, wherein the adherence data comprises a timestamp identifying when the cap was removed from the container. Reflected light data obtained by the sensor is sent to a processor, and the processor uses the data to determine whether the cap has been removed from the container. When the cap is removed from the container, the processor generates the timestamp.

20 Claims, 9 Drawing Sheets

DEVICE FOR TRACKING MEDICATION ADHERENCE

CROSS-REFERENCE TO RELATED APPLICATIONS

The present application claims priority to U.S. Provisional Patent Application No. 62/990,442 filed Mar. 16, 2020, and entitled "DEVICE FOR TRACKING MEDICATION ADHERENCE," which is hereby incorporated by reference in its entirety as if fully set forth herein.

BACKGROUND

Field of the Art

This invention generally relates to an apparatus that can be attached to a conventional medication bottle cap, and that is configured for tracking a user's adherence to a medication schedule. More specifically, the invention relates to a device that attaches to medication bottle caps that and notifies a user when it is time to take the medication and tracks when the medication bottle is opened.

Discussion of the State of the Art

Prior art systems and methods for reminding a patient to take a medication and/or tracking a patient's compliance with a medication schedule are unreliable and prohibitively expensive. For example, automated medication reminder and tracking systems typically require specialized equipment and specialized software to track medication adherence data and remind a user to take a medication. However, most clinicians and patients do not have the budgets to purchase expensive, specialized equipment necessary to use these systems. Indeed, because of these and other constraints, the adoption and usage rate for these types of systems is abysmally low.

Prior art medication tracking and reminder devices that include a sensor for determining when a bottle cap is removed from a bottle are unreliable, cumbersome, and expensive. For example, devices having a mechanical sensor for detecting bottle cap removal may break easily or may fail after several uses. Devices having optical sensors for detecting bottle cap removal may not work well in low-light conditions and may be unreliable when ambient light conditions change rapidly. Some of these prior art medication tracking and reminder devices have several parts, thus increasing their complexity, chances of failure, and opportunities for user error. For example, some prior art devices may include a reflective sticker that is required to be attached to the bottle and/or the cap in order for the sensor to function properly. If the sticker is not attached or improperly attached, the device will not work properly. Further, these devices may be built in to a medication bottle and/or bottle cap, and therefore may only be compatible with caps or bottles of a certain size.

SUMMARY

The inventive apparatus disclosed herein is a reliable, low-cost solution for tracking medication adherence data and for reminding a user when it's time to take a medication. In one embodiment of the invention, the inventive apparatus is as a tracking device that couples to the underside of traditional prescription bottle caps of various shapes and sizes. Generally, the inventive apparatus includes an infrared proximity sensor that determines when the cap is removed from the bottle. Data regarding the cap removal event (i.e., adherence data) is saved in the memory of the apparatus and communicated to an external computing device when possible. By using an infrared proximity sensor, the inventive apparatus is not subject to changing ambient light conditions, and is thus reliable even in low-light conditions.

In another embodiment, the inventive apparatus is equipped with a light source and is configured to emit a light signal to notify a user of a condition. For example, the light signal may be a blinking green light to notify a user that it is time to take a medication, or a blinking red light to notify a user that it is not time to take a medication.

In yet another embodiment, the inventive apparatus is equipped with wireless communication technology so that a user, such as patient, pharmacist, doctor, or the like, may program the tracking device and review data from the tracking device through a mobile application or other software program.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

FIG. 3B' is a close up, detailed, cross-sectional view of a portion of the medication bottle and bottle cap, in accordance with one embodiment of the invention.

DETAILED DESCRIPTION

The inventors have conceived, and reduced to practice, an apparatus, a system, and a method for tracking adherence to a medication schedule. Various embodiments of the inventive apparatus, system, and method are disclosed herein, including numerous alternative arrangements. However, it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

Conceptual Architecture

Disclosed herein is a medication adherence tracking device that can be attached to a conventional bottle cap for a medication bottle. The tracking device generates medication adherence data and transmits the data to an external computing device for review by a user such as a patient, pharmacist, doctor, pharmaceutical company, or the like. The tracking device is equipped with a sensor to detect when the cap has been removed and disconnected from the bottle, indicating that the medicine was taken. The tracking device may be programmed with a dosing schedule and may be configured to emit light to notify a user when it is time to take the medication based on the dosing schedule.

Figure 1A:
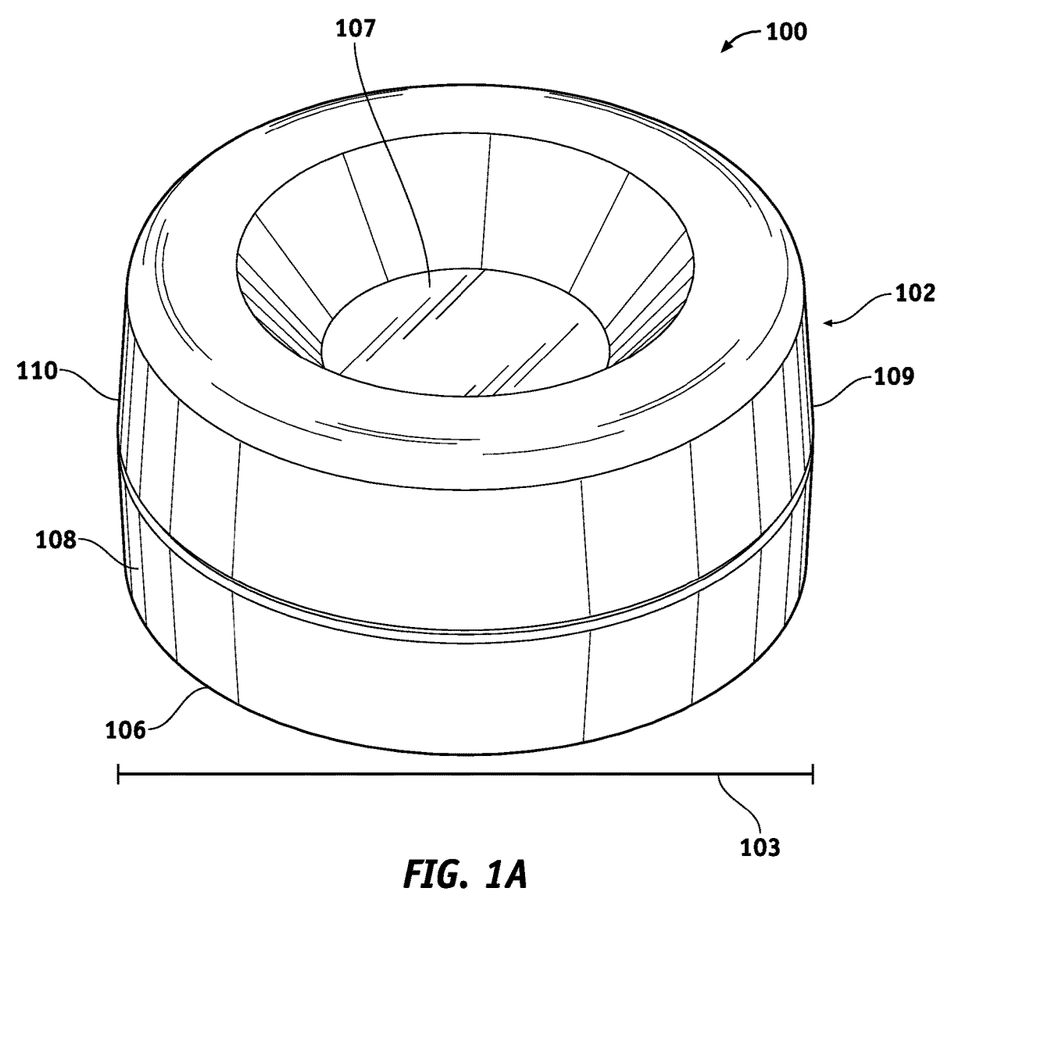
FIG. 1A is a bottom perspective view of an exemplary medication adherence tracking device, in accordance with one embodiment of the invention.
Figure 1B:
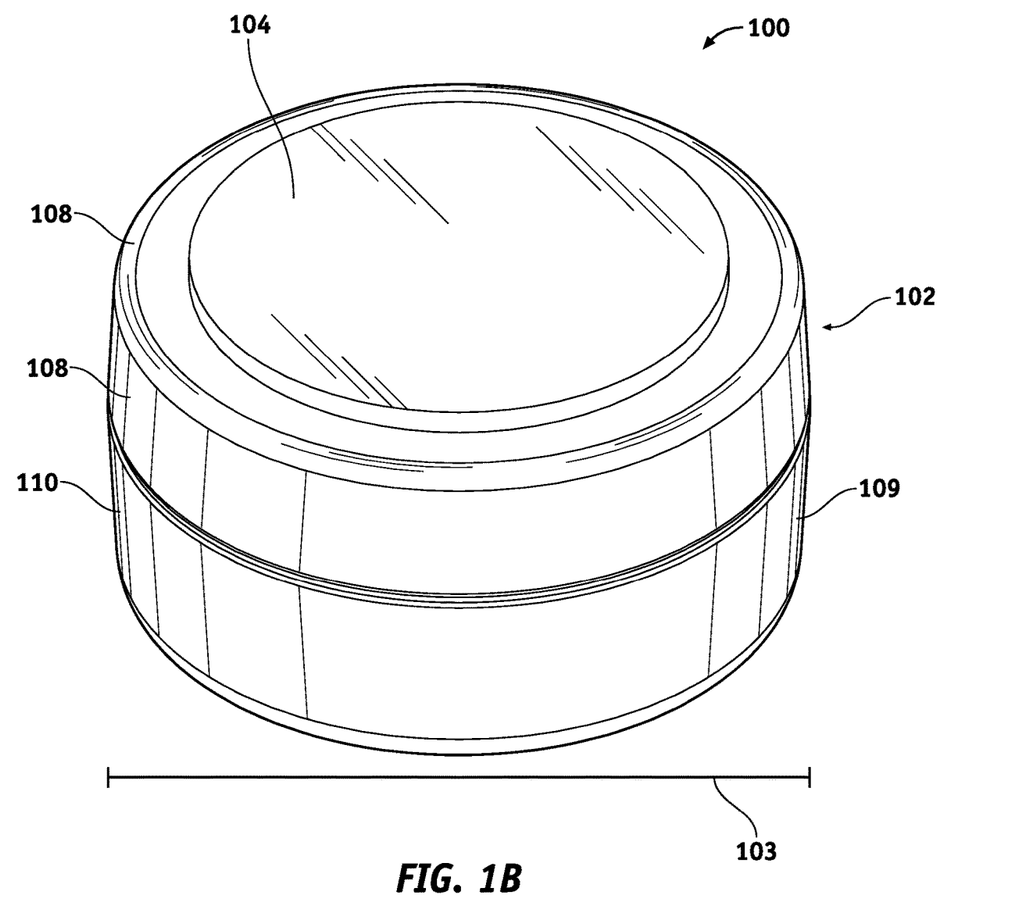
FIG. 1B is a top perspective view of the exemplary medication adherence tracking device, in accordance with one embodiment of the invention.

A medication adherence tracking device 100 is depicted in FIGS. 1A and 1B. In general, the device 100 is configured to alert a user when it is time to take his/her medicines and to log the time when this medicine was actually taken. Such medication adherence data is saved on the device 100 and/or communicated to an external computing device.

The device 100 is sized and shaped to be attached to a lid or cap of a conventional prescription medicine bottle of any size. For example, the bottle cap may have an outer diameter between 32 mm and 50 mm, and may have an inner diameter of at least 27.5 mm. As such, the device 100 may have an outer diameter 103 that is less than the inner diameter of the bottle cap to which the device 100 is to be attached. Preferably, the outer diameter 103 of the device 100 is small enough that the device 100 is universal and can be attached to a bottle cap having any size. For example, the outer diameter 103 of the device 100 may be less than 26 mm. The device 100 is preferably attached to the internal side of the bottle cap. However, one of ordinary skill in the art would readily understand that the tracking device 100 may alternatively be configured to be attached to the inside of a medication bottle.

The tracking device 100 includes a housing 102 and an adhesive layer 104 on an outer surface of the housing 102. In this embodiment, the adhesive layer 104 is on the top surface 106 of the housing 102, but the adhesive layer 104 may alternatively be disposed on any other location on the housing 102 that facilitates the device 100 being attached to a medication bottle cap via the adhesive layer 104. The adhesive layer 104 may, for example, be similar to double-sided tape where one side of the adhesive layer 104 is coupled to the housing 102, and the other side of the adhesive layer 104 is covered with a removable paper backing that can be removed by the user to expose the other side of the adhesive layer 104 before attaching the device 100 to the medication bottle cap.

The housing 102 includes an upper housing portion 108 attached to a lower housing portion 110. The upper housing portion 108 may be permanently or releasably coupled to the lower housing portion 110 with any known attachment mechanism. For example, the upper housing portion 108 may be threadably coupled to the lower housing portion 110, so that the upper and lower portions 108, 110 can be unscrewed to open the housing 102 and access the device components within the housing 102 and then screwed back together to close the housing 102. Alternatively, the upper housing portion 108 and the lower housing portion 110 may be attached together by glue, welding, tape, snap-fit attachment, or the like. In another embodiment, the housing 102 may be formed as one unitary piece with the components sealed inside. In another alternative embodiment, the housing 102 may include a cup-shaped portion and a lid permanently or releasably attached to the cup-shaped portion. The housing 102 may be sealed shut in a manner that prevents moisture from entering the housing 102. As such, the tracking device 100 may be used in a medication bottle that holds a liquid medication.

The housing 102 includes clear, transparent, or translucent portions that allow visible light to pass through the housing 102. For example, a bottom surface of the housing 102 includes a transparent or translucent window 107, and sidewalls 109 of the housing 102 may be transparent or translucent. However, in other exemplary embodiments, the transparent or translucent portions may be located in other areas of the housing 102, or the entire housing 102 may be translucent or transparent. A light source disposed within the housing 102 may thus emit visible light through the clear, transparent, or translucent portions 107, 109 of the housing 102 in order to notify a user of a condition. For example, the condition may be that it is time for the user to take a medication, and the light source may emit a blinking light to notify the user to take the medication.

Figure 2A:
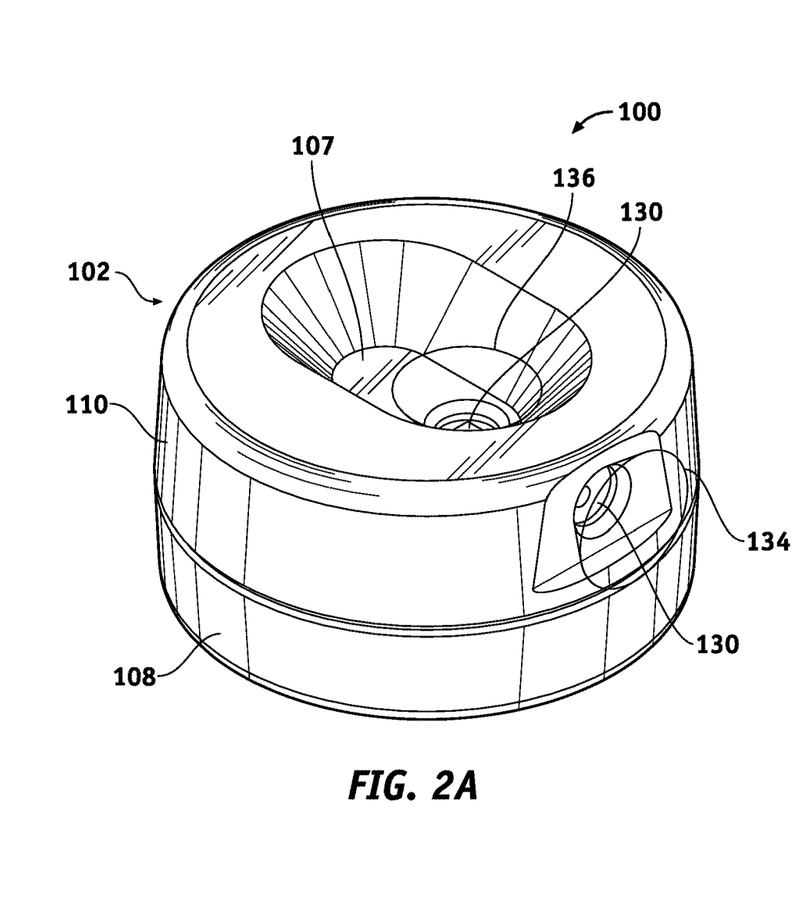
FIG. 2A is a bottom perspective view of an exemplary medication adherence tracking device, in accordance with one embodiment of the invention.
Figure 2B:
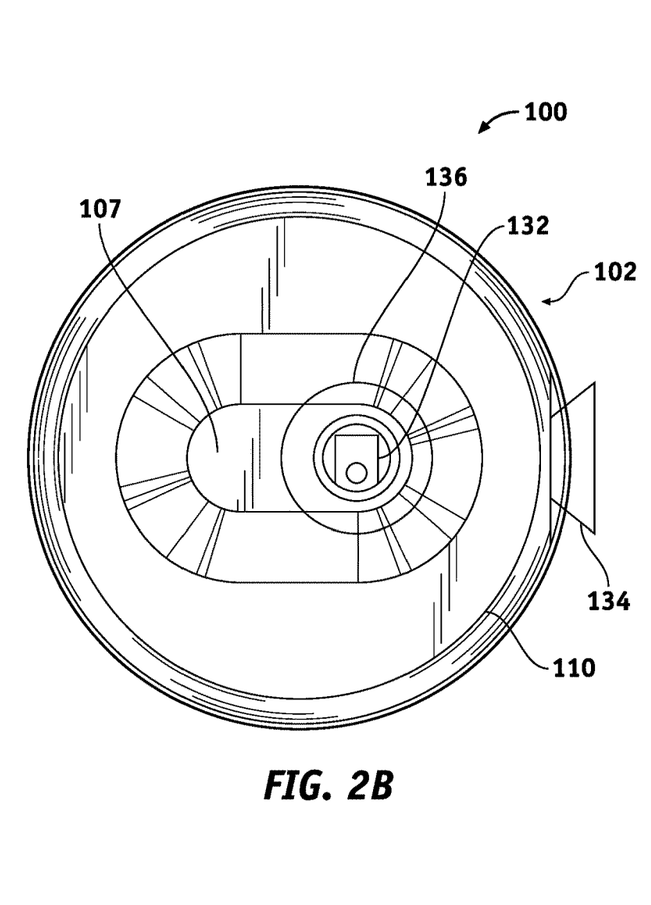
FIG. 2B is a plan view of the bottom surface of the exemplary medication adherence tracking device, in accordance with one embodiment of the invention.
Figure 2C:
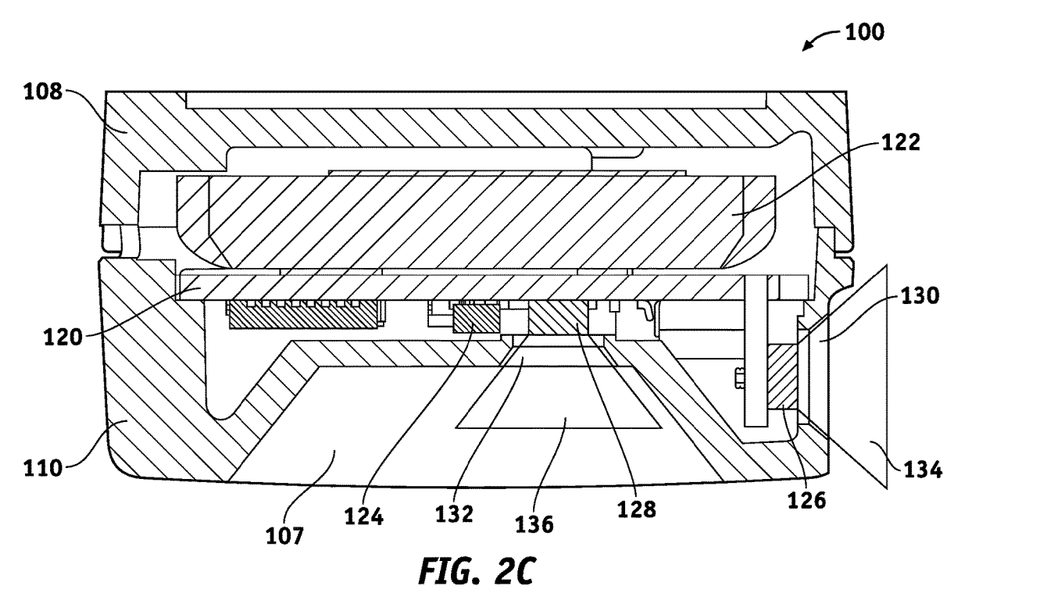
FIG. 2C is a cross-sectional view of an exemplary medication adherence tracking device, in accordance with one embodiment of the invention.
Figure 2D:
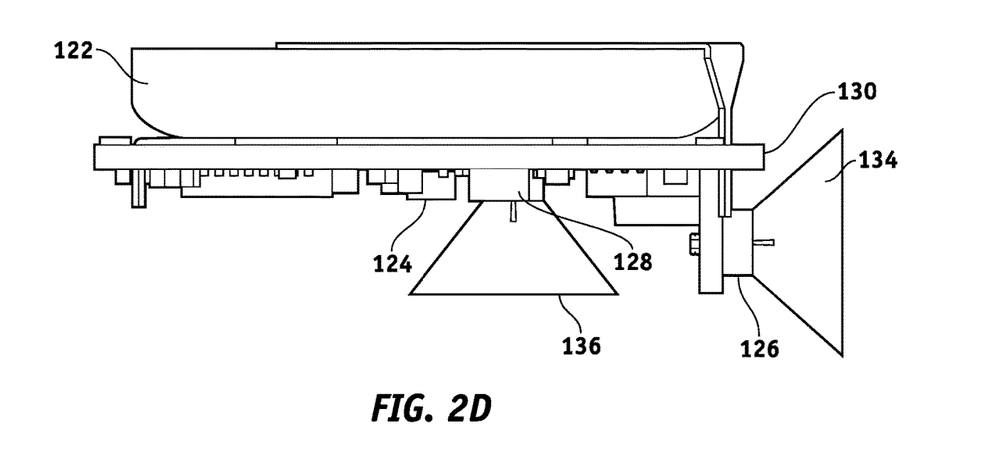
FIG. 2D is a cross-sectional view of the internal components of an exemplary medication adherence tracking device, in accordance with one embodiment of the invention.

Further details of the tracking device 100 will be discussed with reference to FIGS. 2A-2D. The components disposed inside the housing 102 are shown in FIGS. 2C and 2D. In general, a printed circuit board (PCB) 120, power source 122, and light source 124 are contained within the housing 102. Other components, discussed in further detail below, may also be contained in the housing 102.

The device 100 includes at least one proximity sensor for detecting when a medication bottle cap has been removed from a medication bottle. In the embodiment shown in FIGS. 2A-2D, the device 100 includes two proximity sensors. However, it should be well understood that the tracking device 100 may alternatively have only one proximity sensor. A wall detection proximity sensor 126 is configured to detect a wall of a medication bottle. A bottom surface proximity sensor 128 is configured to detect the bottom surface of the medication bottle and/or the pills or liquid contained in the medication bottle. The housing 102 includes openings 130 and 132 adjacent to the proximity sensors 126 and 128 in order to allow signals 134, 136 from the proximity sensors 126, 128 to be emitted from the housing 102 without interference. In this embodiment, the openings 130, 132 are in the lower housing portion 110, but the openings 130, 132 could alternatively be located in the upper housing portion 108, depending on where the proximity sensors 126, 128 are located. That is, the through holes 130, 132 may be located anywhere in the housing 102 that is adjacent to the proximity sensors 126, 128 disposed within the housing 102 in order to facilitate signals 134, 136 being emitted and received by the sensors 126, 128. The device 100 may further include a seal (not shown) disposed between each one of the proximity sensors 126, 128 and the corresponding openings 130, 132 in order to prevent moisture from entering the housing 102 and damaging the components therein.

The proximity sensors 126, 128 may be configured to periodically scan the wall or bottom of the medication bottle at predetermined intervals. Alternatively, in order to reduce power consumption, the proximity sensors 126, 128 may have active and inactive modes, where the proximity sensors 126, 128 only scan the medication bottle wall or bottom during the active mode. The tracking device 100 may further include a motion detector (discussed in further detail below) configured to detect when the medication bottle is moving and to activate one or both of the proximity sensors 126, 128 when motion is detected. Although two proximity sensors 126, 128 are depicted in the embodiments herein, the device 100 may alternatively include only one of the sensors 126 or 128. In yet another embodiment, the tracking device 100 includes three or more proximity sensors for redundancy in case one or more of the proximity sensors fails.

The proximity sensors 126, 128 are preferably infrared proximity sensors that emit and receive an infrared signal. In one embodiment, the sensors 126, 128 are laser infrared proximity sensors. Infrared sensors are advantageous over optical sensors because fluctuations in ambient light do not affect the reliability of the infrared proximity sensors.

The power source 122 may be a battery that is rechargeable or non-rechargeable. In one embodiment, the power source 122 is a non-rechargeable disposable battery that has a battery life of at least 3 months. The power source 122 may be permanently attached within the housing 102 or may be detachably coupled so that it can be replaced when the power is depleted. The power source 122 provides energy and/or power to any element of the tracking device 100 that may use energy and/or power.

The light source 124 is preferably an energy efficient light source that consumes relatively little power, such as an LED. For example, the light source 124 may be an LED that emits red, green, and/or yellow light. The light source 124 is positioned to emit light through a clear, transparent, or translucent portion of the housing 102, such as the window 107, so that the light shines into the bottle when the cap is on the bottle. When light is emitted, a user can see the light due to the translucent material of a conventional prescription bottle. As such, the light source 124 can be configured to emit light having different colors and/or patterns to notify a user of a particular condition. For example, the light source 124 can be configured to emit a blinking green light when it is time for the user to take a medication. In another example, the device 100 is equipped to detect movement and the light source 124 is configured to emit red light when motion is detected and it is not time for the user to take a medication. In yet another example, the light source 124 is configured to emit a blinking yellow light when the battery is low. The light source 124 may emit light that blinks at any desired interval. For example, the light may blink every 2-30 seconds. Preferably, the light pulses are short so that energy consumption and heat accumulation are limited. In other words, the light is on for a relatively short amount of time and the time between light pulses is relatively long in order to limit energy consumption and heat accumulation. The light source 124 may alternatively be configured to emit a steady light signal rather than a pulsing light signal. The color and pattern of the light signal can be customized by a user through a mobile application or other similar user interface that is in communication with the tracking device 100.

Figure 3A:
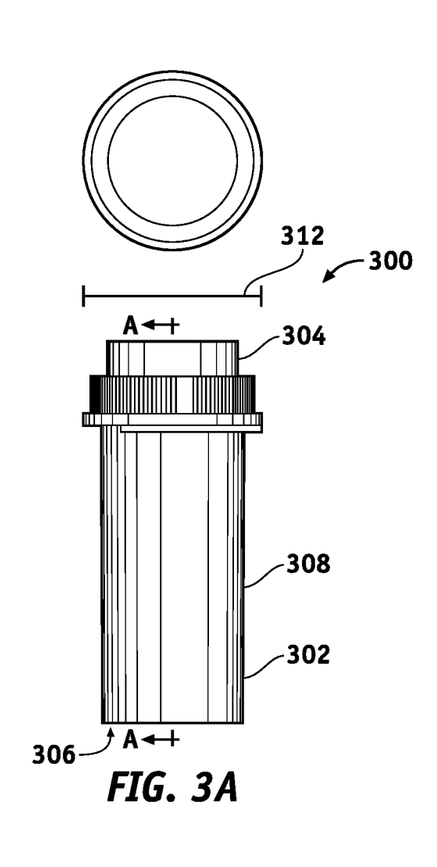
FIG. 3A is a side view of a conventional medication bottle and bottle cap.

FIGS. 3A-3D depict a system 300 that includes a medication bottle 302, a bottle cap 304, and the tracking device 100 attached to the bottle cap 304. FIG. 3A illustrates the medication bottle 302 with the cap 304 attached thereto. The bottle 302 and cap 304 are preferably a conventional prescription bottle and cap such as those that are already being widely used in pharmacies, hospitals, doctor's offices, etc. The medication bottle 302 is cylindrically shaped and has a bottom surface 306, a cylindrical sidewall 308, and an open top 310 (shown in FIGS. 3C and 3D). Medication bottles are typically translucent and have an orange or light brown hue that blocks UV light, but allows enough visible light through so that the contents of the bottle can be seen from outside of the bottle without opening the bottle. Further, as discussed above, light emitted by the light source 124 can be seen through the translucent bottle. The bottle 302 and cap 304 may have any standard size and shape. For example, the outer diameter 312 of the cap 304 may be 32-50 mm. Typically, the top portion of the bottle 302 includes outer threads 314 (shown in FIGS. 3C and 3D) and the inner surface of the cap 304 includes inner threads, so that the cap 304 can be threadably coupled to the bottle 302.

Figure 3B:
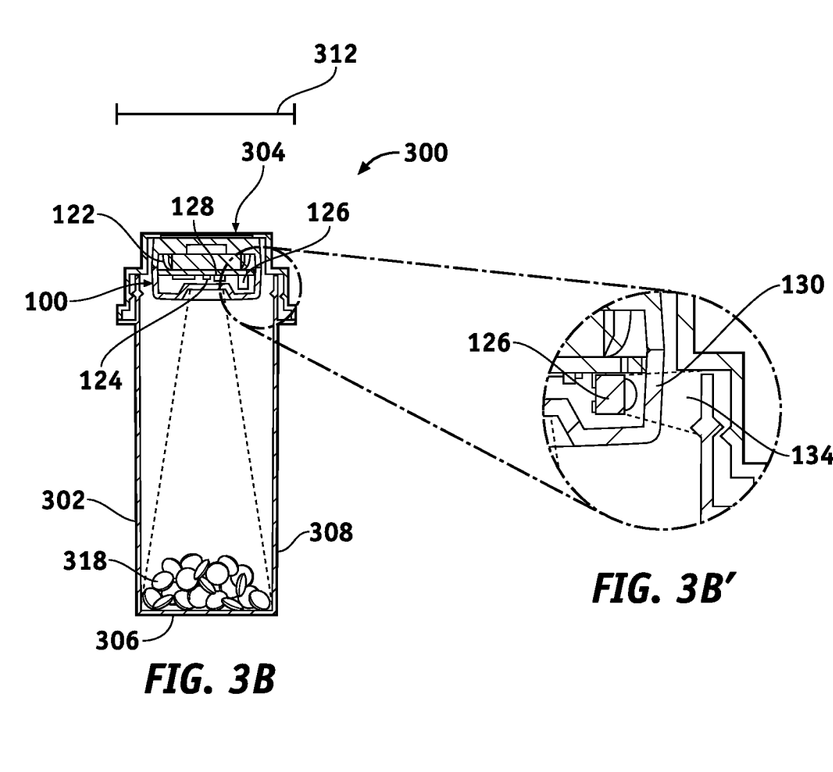
FIG. 3B is a cross-sectional view along lines A-A of FIG. 3A of a conventional medication bottle and bottle cap having an exemplary medication adherence tracking device attached thereto, in accordance with one embodiment of the invention.

As shown in the cross-sectional view of FIG. 3B, the medication adherence tracking device 100 depicted in FIGS. 1A-2D is attached to the underside of the bottle cap 304. The adhesive layer 104 couples the device housing 102 to the inside surface of the cap 304.

The wall detection proximity sensor 126 is configured to detect the proximity between the wall 308 of the medication bottle 302 and the device 100. As shown in the magnified view in FIG. 3B', upon activation, the wall detection proximity sensor 126 emits light 134 through an opening 130 in the housing 102 towards the wall 308 of the medication bottle 302. The sensor 126 is configured to detect how much light is reflected back and determine, based on the amount of reflected light, the proximity between the wall 308 of the bottle 302 and the sensor 126. In this manner, the wall detection proximity sensor 126 detects whether the cap 304 is coupled to the bottle 302. In one example, the wall detection proximity sensor 126 is an infrared proximity sensor, and the light that is emitted and reflected is infrared light.

Similarly, the bottom surface proximity sensor 128 is configured to determine the proximity between the bottom surface proximity sensor 128 and the bottom surface 306 of the medication bottle 302, or between the bottom surface proximity sensor 128 and the pills 318 contained in the bottle 302. Upon activation, the bottom surface proximity sensor 128 emits light and detects an amount of light that is reflected back. Based on the amount of reflected light, the proximity between the bottom 306 of the medication bottle 302 and the sensor 128 can be determined. In this manner, the bottom surface proximity sensor 128 determines whether the cap 304 is coupled to the bottle 302. In one example, the bottom surface proximity sensor 128 is an infrared proximity sensor configured to emit infrared light towards the bottom 306 of the bottle 302 through an opening in the housing 102.

The device 100 may be equipped with either the wall detection proximity sensor 126 or the bottom surface proximity sensor 128, or may be equipped with both sensors 126 and 128. The sensors 126, 128 may be programmed to activate periodically at pre-determined intervals. Alternatively, in order to conserve power, the sensors 126, 128 may have an active mode and an inactive mode. When movement of the medication bottle 302 is detected, the sensors 126, 128 may be activated, as discussed in more detail below.

The proximity sensors 126, 128 are preferably infrared-based proximity sensors to eliminate the effects of varying ambient light on detecting the bottle wall 308 or bottom surface 306. Because the sensors 126, 128 use infrared radiation (or light), fluctuation in ambient (visible) light will not affect the ability of the sensors 126, 128 to detect the wall 308 or bottom surface 306 of the medication bottle 302. Infrared-based proximity sensors emit and receive signals that are in the infrared range of wavelengths rather than the visible spectrum. As such, even if a user is taking medication at night in the dark, or in low-light conditions, the infrared proximity sensors 126, 128 will still be able to detect when the cap 304 is removed from the bottle 302. In one embodiment, the infrared proximity sensors 126, 128 are laser infrared sensors.

Figure 3C:
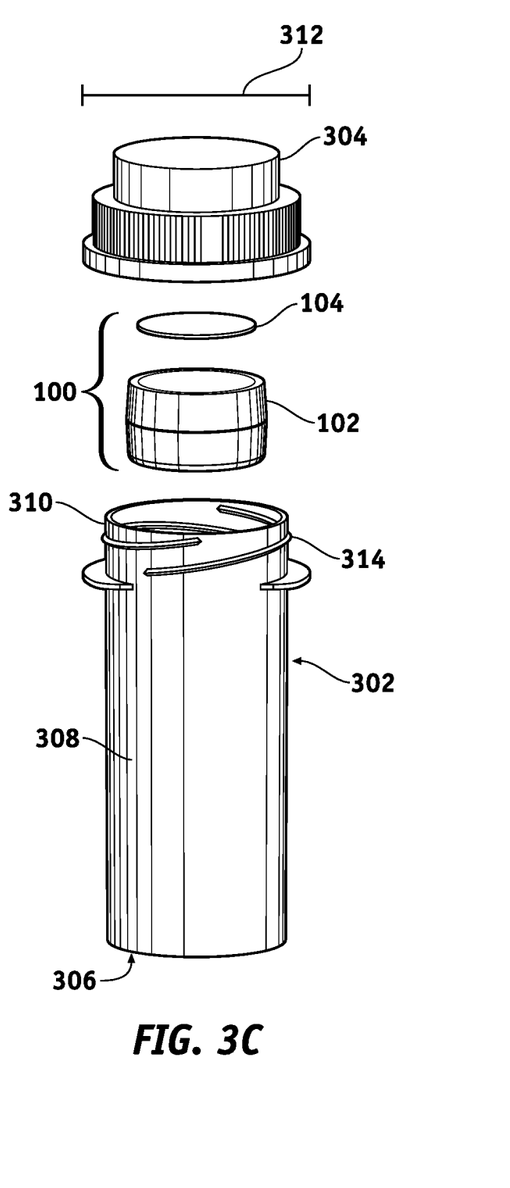
FIGS. 3C and 3D are exploded views of a conventional medication bottle and bottle cap and an exemplary medication adherence tracking device to be attached to the bottle cap, in accordance with one embodiment of the invention
Figure 3D:
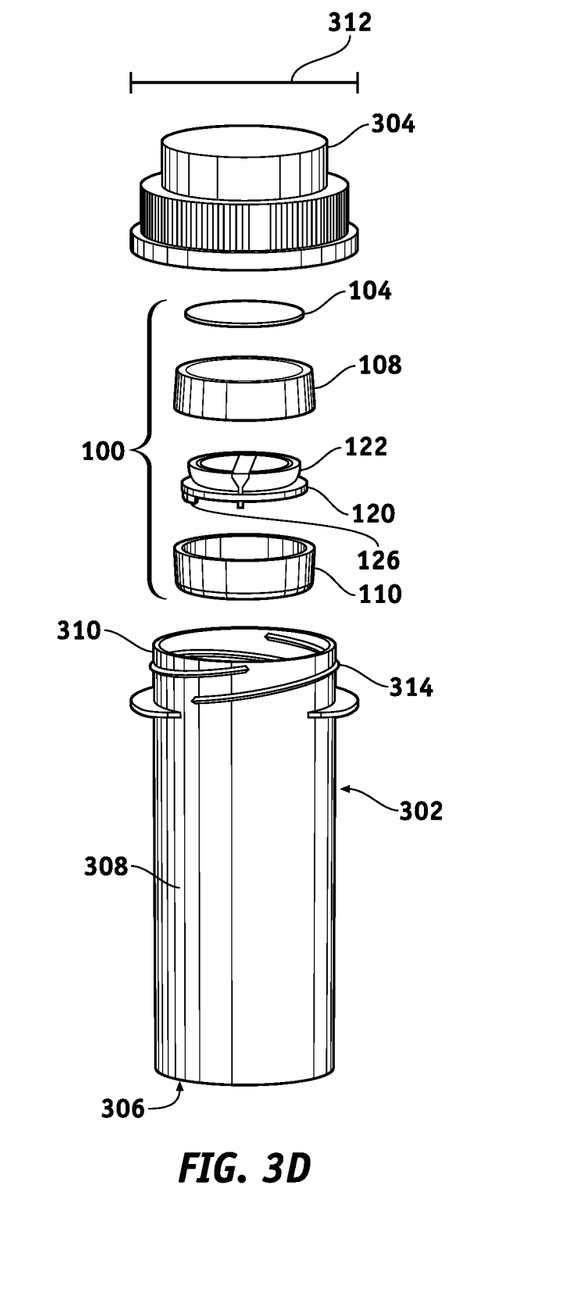

FIG. 3C is an exploded view showing the medication bottle 302 having the open top end 310 and outer threads 314, the medication bottle cap 304, and the medication adherence tracking device 100 including the housing 102 and the adhesive layer 104, and. The housing 102 is coupled to the inside surface of the bottle cap 304 with the adhesive layer 104. The device 100 is sized and shaped to be compatible with any size of bottle cap 304. Similarly, FIG. 3D is an exploded view depicting the top housing portion 108, the bottom housing portion 110, and the components disposed inside the housing 102. The components include the PCB 120, the power source 122, the wall proximity sensor 126, as well as other components discussed above that are not depicted in FIG. 3D.

Figure 4:
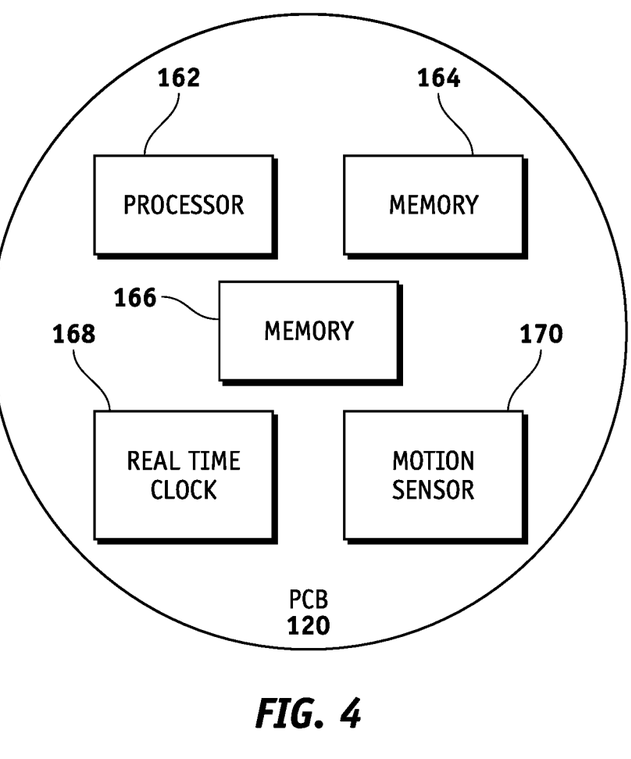
FIG. 4 is a block diagram of the components of a printed circuit board for the exemplary medication adherence tracking device, in accordance with one embodiment of the invention.

As shown in FIG. 4, the PCB 120 of the device 100 includes a processor 162, a memory 164, a transceiver 166, a real time clock calendar 168, and a motion sensor 170. The memory 164 is configured to store data, such as a dosing schedule and captured medication adherence data. Medication adherence data may include timestamps that indicate dates and times when the bottle cap 304 was removed from the bottle 302.

The transceiver 166 includes both a transmitter and a receiver for two-way wireless communication with an external computing device. The transceiver 166 receives data from, and transmits data to, the external computing device. For example, the dosing schedule may be uploaded to the tracking device 100 via the transceiver 166 and then stored in the memory 164. In another example, the transceiver 166 transmits medication adherence data to the external computing device. The transceiver 166 may include wireless communication technology, such as Bluetooth Low Energy.

Alternatively, the device 100 may include only a transmitter or only a receiver, rather than the transceiver 166.

The clock 168 may track a current time. The respective dosing schedule and the current time may be used by the processor 162 to determine if it is time to take a medication or not.

The processor 162 is configured to determine when the bottle cap 304 is removed from the bottle 302, generate a timestamp to reflect the removal event, and determine whether the current time is within a dosing window in accordance with the dosing schedule stored in the memory 164.

In order to determine whether the cap 304 was removed from the bottle 302, the processor 162 receives reflected light data from at least one of the proximity sensors 126, 128 and processes the reflected light data. The processor 162 makes the determination by comparing the reflected light data to reflected light data that was previously received from the proximity sensors 126, 128. If the comparison reveals a change in the reflected light data that is greater than a threshold amount, then the processor 162 determines that the cap 304 was removed from the bottle 302. If the comparison reveals that the change in the reflected light data is less than or equal to a threshold amount, then the processor 162 determines that the cap 304 was not removed from the bottle 302. In other words, when the cap 304 is attached to the bottle 302, the amount of reflected infrared light stays relatively constant so that when the proximity sensor 126, 128 receives an amount of reflected light, the amount is approximately equal to the amount of reflected light that was previously received while the cap 304 was attached to the bottle 302. However, when the cap 304 is removed from the bottle 302, there is a large change in the amount of reflected infrared light that is received by the proximity sensor 126, 128. Thus, when a change in the amount of reflected light exceeds a threshold amount, the cap 304 has most likely been removed from the bottle 302, and the processor 162 generates a timestamp to reflect the cap removal event. Adherence data including the timestamp is saved in the memory 164 and/or transmitted to an external computing device through the transceiver 166 in order to monitor compliance and update the dosing schedule.

Figure 5:
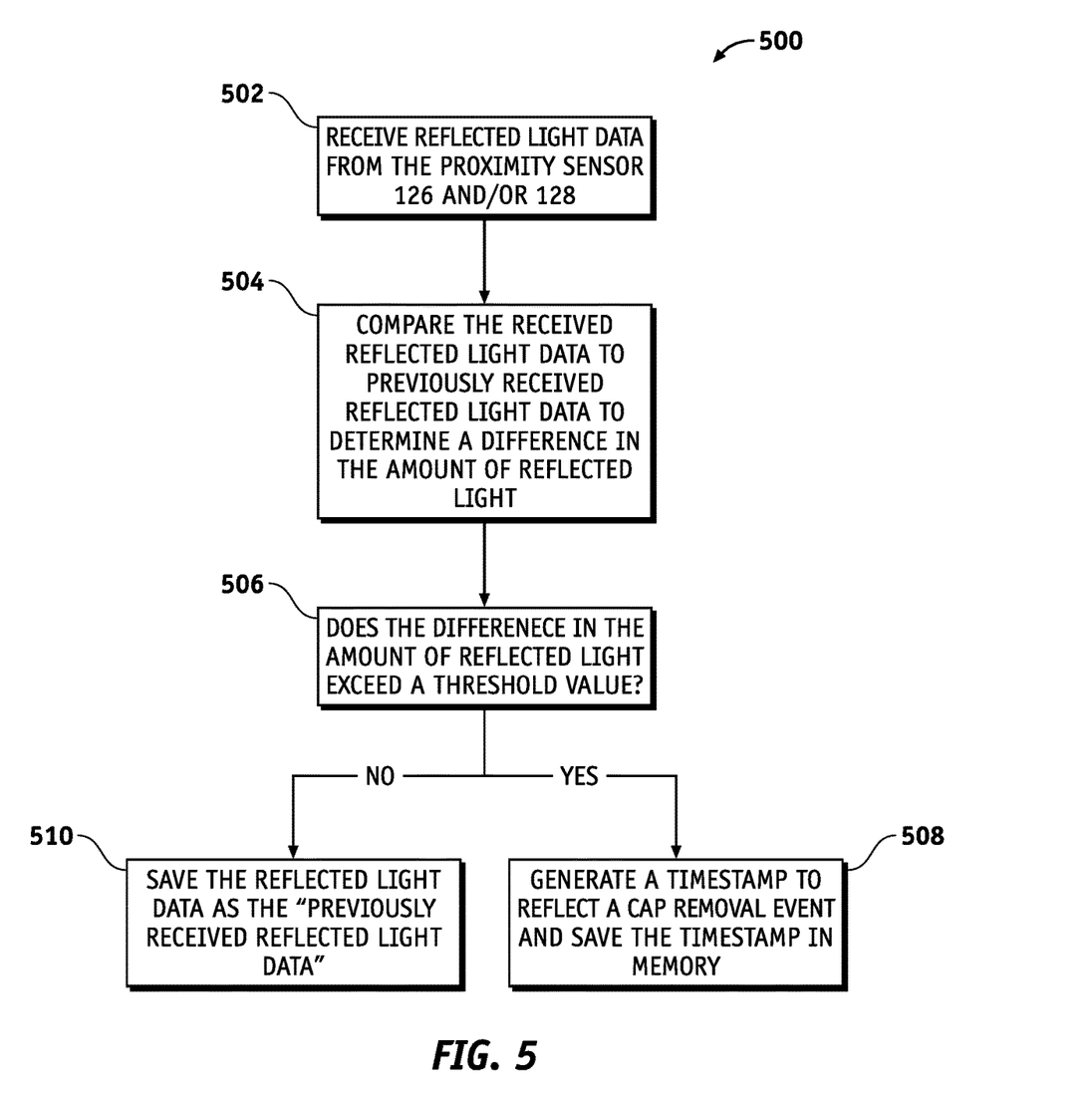
FIG. 5 is a flow chart of a method for determining whether a bottle cap has been removed from a bottle, in accordance with one embodiment of the invention.

FIG. 5 depicts the steps taken by the processor 162 in a method 500 for determining whether the cap 304 was removed from the bottle 302. First, in step 502, the processor 162 receives reflected light data from the proximity sensor 126 and/or 128. Next, in step 504, the received reflected light data is compared to reflected light data that was previously received in order to determine a difference between the current amount of reflected light and the previous amount of reflected light. If the difference exceeds a threshold value, as determined in step 506, then the cap 304 has presumably been removed from the bottle 302 and the processor 162 generates a timestamp in step 508. In this manner, every time the cap 304 is removed from the bottle 302, adherence data is generated and saved in the memory 164, and is eventually transmitted to an external computing device. The adherence data, including the timestamp, is saved in the memory 164 and/or transmitted to an external computing device. If, in step 506, it is determined that the difference does not exceed a threshold value (e.g., the amount of reflected light remains the same), then the cap 304 has presumably not been removed from the bottle 302 and the reflected light data received in step 502 is saved as the "previously received reflected light data" to be compared with subsequently received reflected light data.

In one embodiment, the method 500 occurs after the motion sensor 170 detects movement. That is, the proximity sensors 126, 128 are only activated after the motion sensor 170 detects that the medication bottle cap 304 is moving. In an alternative embodiment, the processor 162 receives data from the proximity sensor(s) 126 and/or 128 and from the motion sensor 170 and uses this data to determine whether the cap 304 was removed.

In one embodiment, the motion sensor 170 is a 9-axis inertial management unit (IMU). A 9-axis IMU combines a 3-axis accelerometer, a 3-axis gyroscope, and a 3-axis compass to determine the spatial movement of the bottle cap 304 with respect to time and trigger a cap removal signal accordingly. In this embodiment, a sequence of movements, such as rotation around the z-axis for several turns followed by displacement along the z-axis would be detected by the motion sensor 170 and then processed by the processor 162 to determine that the cap was removed. In this embodiment, the data provided by the motion sensor 170 may be used in addition to, or instead of, data from the proximity sensors 126, 128 to determine whether the bottle cap 304 was removed from the bottle 302.

The processor 162 is further programmed to determine whether the current time is within a dosing window. A dosing schedule saved in the memory 164 includes dosing windows wherein the user should take the medication if the current time falls within one of the dosing windows. The processor 162 may retrieve a dosing schedule from the memory 164. The processor 162 may retrieve a current time from the clock 168. The processor 162 may compare the dosing schedule to the current time to determine if it is time to take a pill.

In one embodiment, the processor 162 may execute in response to detection of movement by the motion sensor 170. That is, the processor 162 executes the steps to determine whether the current time is within a dosing window each time the motion sensor 170 detects movement. Alternatively, the processor 162 is configured to periodically execute the steps to determine whether the current time is within a dosing window. That is, the processor 162 automatically activates at pre-determined intervals, such as every 15-30 minutes.

The pattern and/or color of light emitted by the light source 124 is controlled by the processor 162 to convey particular meanings or warnings. The light source 124 may react to a signal provided by the processor 162. The light source 124 may comprise a setting associated with a time to take a pill. The light source 124 may comprise a setting associated with a time not to take a pill. A setting may comprise a position (e.g., "on", "off", etc.), a light pattern (e.g., every LED illuminated, every other LED illuminated, every third LED illuminated, etc.), a flashing pattern (e.g., blinking, two fast flashes followed by a long pause, etc.), a color (e.g., red, green, etc.), or the like, and/or any combination of the foregoing. For example, the light source 124 may display a green color in response to a signal indicative of a time to take a pill. As another example, the light source 124 may display a red color in response to a signal indicative of a time not to take a pill. The light source 124 may illuminate in response to the motion sensor 170 detecting a movement of the tracking device 100. For example, the light source 124 many emit a green light if the motion sensor 170 detects movement and it is time for the user to take the medication. Similarly, the light source 124 may emit a red light if the motion sensor 170 detects movement and it is not time for the user to take the medication.

The motion sensor 170 detects that the bottle 302, with the cap 304 thereon, has moved. Motion detected by the motion sensor 170 may indicate that the bottle 302 is being picked up by the user with the intention of removing the cap 304 in order to take the medication. The motion sensor 170 may be configured to activate the proximity sensors 126, 128 and the processor 162 when motion is detected, as discussed above. When activated, the proximity sensors 126, 128 emit and receive signals to determine whether the cap 304 has been removed from the bottle 302. Thus, power consumption is reduced by enabling the infrared radiation only when the bottle 302 moves. The motion sensor 170 may be an accelerometer, vibration sensor, tilt sensor, or the like.

In another embodiment, the motion sensor 170 causes a dosing schedule to be checked. When the motion sensor 170 detects movement, the processor 162 checks the dosing schedule and instructs the light source to emit an appropriate light signal.

Figure 6:
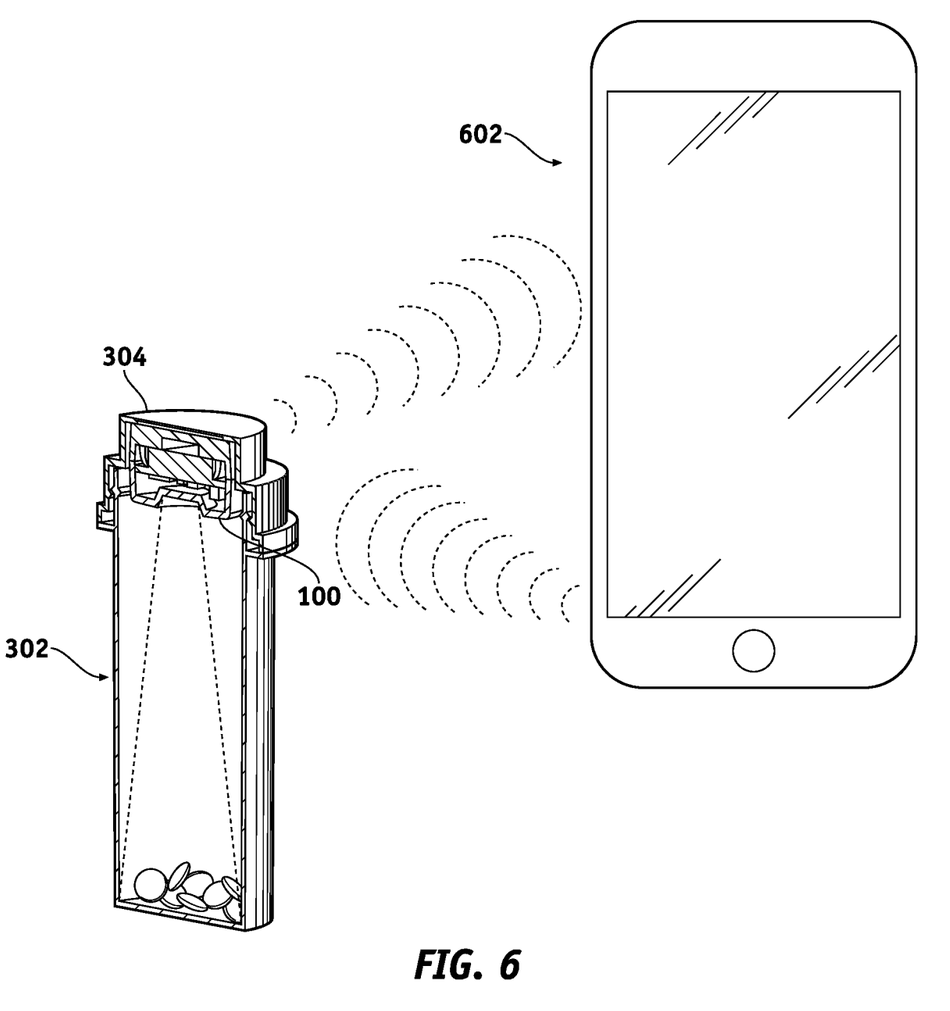
FIG. 6 is a plan view of an exemplary medication adherence tracking device, in accordance with one embodiment of the invention, disposed within a conventional medication bottle cap and communicating with an external computing device.

In one embodiment, as shown in FIG. 6, the device 100 is in communication with an external computing device 602. Although the external computing device 602 is depicted as being a smartphone, it will be readily understood by a person of ordinary skill in the art that the external computing device 602 may alternatively be any other type of computing device, such as a laptop computer, desktop computer, tablet, smartwatch, or the like. When the tracking device 100 and the external computing device 602 are in communication (e.g., when the devices 100, 602 are in close enough range for wireless communication and connection is established), the cap removal event information stored on the tracking device 100 is communicated to the external computing device 602 and/or the external computing device 602 transmits the dosing schedule or changes to the dosing schedule to the tracking device 100.

A user may communicate with the tracking device 100 through a mobile application installed on the external computing device 602, or through an online application that can be accessed through the external computing device 602. The mobile or online application provides a user interface through which a user may program the tracking device 100 or review information obtained from the tracking device 100. For example, a pharmacist may program the tracking device 100 with patient information and a dosing schedule by using the application on the external computing device 602. In another example, a doctor, pharmacist, or patient may use the computer application to review cap removal event data and/or adherence data that is communicated from the tracking device 100 to the external computing device 602. In yet another example, a patient may use the mobile or online application to modify whether or not they took their medication properly to prevent accidental miscalculations. That is, if the patient misses a dose or does not take the medication on time, the patient can use the online or mobile application to input that information. The online or mobile application allows the patient to easily input their own medications and schedules, thereby reducing the overall complexity of the process. Further, a user may specify the configuration for the LEDs through the online or mobile application. The computer application associated with the tracking device 100 may be installed on several external computing devices so that several different users have the ability to interact with the tracking device 100.

The skilled person will be aware of a range of possible modifications of the various embodiments described above. Accordingly, the present invention is defined by the claims and their equivalents.

ADDITIONAL CONSIDERATIONS

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A medication adherence tracking device that is configured for being attached to a cap of a medication container, wherein the device comprises:
   an adhesive layer for attaching the device to the cap;
   an infrared proximity sensor for detecting an amount of light that is reflected by at least one of a wall surface and a bottom surface of the medication container; and
   a transmitter for transmitting adherence data to an external computing device, wherein the adherence data comprises a timestamp identifying when the cap was removed from the container.

2. The device of claim 1, further comprising a housing for containing the sensor and the transmitter, wherein the adhesive layer is disposed on an outer surface of the housing.

3. The device of claim 1, further comprising a light source configured to emit a light signal to notify a user of a condition, wherein at least one of a pattern and a color of the light signal depends on the condition to be communicated by the light source.

4. The device of claim 1, further comprising a processor that receives reflected light data from the sensor and processes the reflected light data to determine whether the cap has been removed from the container.

5. The device of claim 4, wherein the reflected light data received by the processor comprises the amount of reflected light that is detected by the sensor.

6. The device of claim 5, wherein the processor determines a change in the amount of reflected light by comparing the received reflected light data to reflected light data that was previously received.

7. The device of claim 6, wherein the processor determines whether the cap has been removed from the container by comparing the change in the amount of reflected light to a predetermined threshold value.

8. The device of claim 1, further comprising a motion sensor for detecting movement of the cap, wherein the motion sensor is in communication with the proximity sensor and is configured to activate the proximity sensor when motion is detected.

9. The device of claim 1, wherein the device is sized and shaped to be attached to any size of cap, and wherein the device has an outer diameter of less than 26 mm.

10. A medication adherence tracking device that is configured for being attached to a cap of a medication container, wherein the device comprises:
an adhesive layer for attaching the device to the cap;
an infrared proximity sensor for detecting an amount of infrared light that is reflected by at least one of a wall surface and a bottom surface of the medication container;
a transmitter for transmitting adherence data to an external computing device, wherein the adherence data includes a timestamp identifying when the cap was removed from the container; and
a processor in communication with the proximity sensor and the transmitter, wherein the processor is configured for determining whether the cap was removed from the container and for generating the timestamp.

11. The device of claim 10, wherein the processor is configured for:
receiving reflected light data from the proximity sensor, wherein the reflected light data includes the amount of light that is reflected;
determining a change in the amount of reflected light by comparing the reflected light data to previous reflected light data that was previously received from the proximity sensor;
comparing the change in the amount of reflected light to a threshold value to determine whether the cap has been removed from the container.

12. The device of claim 11, wherein the processor is configured for:
determining that the change in the amount of reflected light exceeds the threshold value; and
instructing the transmitter to transmit the adherence data.

13. The device of claim 10, further comprising a housing, wherein the proximity sensor, transmitter, and processor are disposed inside the housing, and wherein the adhesive layer is disposed on an outer surface of the housing.

14. The device of claim 10, further comprising a motion sensor in communication with the proximity sensor, wherein the motion sensor is configured for detecting movement of the cap and for activating the proximity sensor when motion is detected.

15. The device of claim 10, wherein the proximity sensor has an active mode and an inactive mode, and wherein the device further comprises a motion sensor for detecting movement of the cap and for switching the proximity sensor from inactive mode to active mode when movement is detected.

16. The device of claim 15, wherein the motion sensor comprises an accelerometer, a gyroscope, a vibration sensor, or a tilt sensor.

17. The device of claim 10, further comprising a battery and a real time clock calendar.

18. The device of claim 10, further comprising a memory, wherein the timestamp generated by the processor is saved in the memory for a predetermined amount of time.

19. The device of claim 14, wherein the processor is configured to receive data from the proximity sensor and from the motion sensor, and to use the data to determine whether the cap has been removed from the bottle.

20. A medication adherence tracking device that is configured for being attached to a cap of a medication container, wherein the device comprises:
an adhesive layer for attaching the device to the cap;
an infrared proximity sensor for detecting an amount of infrared light that is reflected by at least one of a wall surface and a bottom surface of the medication container, wherein the infrared proximity sensor has an active mode and an inactive mode;
a transmitter for transmitting adherence data to an external computing device, wherein the adherence data includes a timestamp identifying when the cap was removed from the container;
a processor in communication with the proximity sensor and the transmitter, wherein the processor is configured for determining whether the cap was removed from the container and for generating the timestamp; and
a motion sensor in communication with the proximity sensor, wherein the motion sensor is configured for detecting movement of the cap and for causing the proximity sensor to switch from the inactive mode to the active mode when motion is detected.

\* \* \* \* \*